US006042814A

United States Patent [19]

Koch et al.

[11] Patent Number: 6,042,814

[45] Date of Patent: Mar. 28, 2000

[54] SULPHONIC ACIDS AND THEIR USE AS UV ABSORBERS

[75] Inventors: Oskar Koch, Göttingen; Roland Langner, Bevern; Alfred Krempel, Holzminden, all of Germany

[73] Assignee: Haarmann & Reimer GmbH, Germany

[21] Appl. No.: 09/061,541

[22] PCT Filed: Oct. 4, 1996

[86] PCT No.: PCT/EP96/04325

§ 371 Date: Apr. 16, 1998

§ 102(e) Date: Apr. 16, 1998

[87] PCT Pub. No.: WO97/14680

PCT Pub. Date: Apr. 24, 1997

[30] Foreign Application Priority Data

Oct. 16, 1995 [DE] Germany ........................... 195 39 623

[51] Int. Cl.[7] ............................... A61K 7/44; A61K 7/42; A61K 7/00; A61K 31/55

[52] U.S. Cl. .............................. 424/60; 424/59; 424/400; 424/401; 514/213

[58] Field of Search ............................... 424/59, 60, 400, 424/401; 514/213; 540/484

[56] References Cited

U.S. PATENT DOCUMENTS

| | | |
|---|---|---|
| 3,637,745 | 1/1972 | Heller . |
| 4,250,315 | 2/1981 | Poncioni ................................ 346/198 |
| 4,654,434 | 3/1987 | Lang et al. . |
| 4,792,609 | 12/1988 | Scholl et al. . |
| 5,474,762 | 12/1995 | Carr et al. . |
| 5,595,215 | 1/1997 | Wallace et al. . |

FOREIGN PATENT DOCUMENTS

| | | |
|---|---|---|
| 207287 | 5/1986 | European Pat. Off. . |
| 1568541 | 1/1975 | Germany . |
| 4203072 | 11/1992 | Germany . |
| 4406024 A1 | 8/1995 | Germany . |

*Primary Examiner*—Shelley A. Dodson
*Attorney, Agent, or Firm*—Brinks Hofer Gilson & Lione

[57] ABSTRACT

Sulphonic acids of formula (I) in which the components and indices have the meanings given in the description, are eminently suitable as u/v absorbers, especially in cosmetic sun-screening agents.

(I)

$R^{5''}$ $R^{4''}$ $R^{5'}$ $R^{4'}$ $R^6$ ${}^4C_m$ ${}^3C_n$ $ZO_3S$ ${}^2C$ $R^5$ N ${}^1C$ $R^3$ $R^4$ $R^2$ $R^1$ X Y

6 Claims, No Drawings

SULPHONIC ACIDS AND THEIR USE AS UV ABSORBERS

The invention relates to new sulphonic acids, a process for their preparation and the use as UV absorbers, in particular in sunscreen compositions.

UV rays are designated, according to wavelength, as UV-A rays (320–400 nm, UV-A-I: 340–400 nm, UV-A-II; 320–340 nm) or UV-B rays (280–320 nm). The following applies very generally: the damaging action of the UV rays on the human skin increases with decreasing wavelength and increasing time of exposure.

UV rays can thus cause skin damage, it being possible for UV-B radiation to cause sunburn (erythema) up to very severe skin burns. Very frequent and unprotected irradiation of the skin with sunlight also leads to a loss of the elasticity of the skin and to increased wrinkle formation, and as a whole to premature ageing of the skin. In extreme cases, pathological skin changes as far as skin cancer can occur.

The UV-A radiation causes a rapid, weak direct pigmentation of the skin. UV-A rays penetrate into deeper layers of the skin and there can accelerate the skin-ageing process. The shorter wavelength UV-A-II radiation assists the formation of sunburn. Furthermore, the UV-A radiation can produce phototoxic or photoallergic skin reactions. Confirmed relationships between UV-A exposure and increased risk of skin cancer exist.

According to the position of their absorption maxima, UV absorbers for cosmetic and pharmacological preparations are divided into UV-A and UV-B absorbers.

For toxicological reasons, nowadays UV absorbers which are applied to the human skin should, if possible, not penetrate the skin.

All sorts of compounds, such as, for example, phenylbenzimidazolesulfonic acid (DE-OS [German Published Specification] 42 03 072), 2-hydroxy-4-methoxybenzophenone-5-sulphonic acid (EP-A 557 089) and terephthalylidene-dibornane-sulphonic acid (DE-OS [German Published Specification] 33 21 679) have already been proposed as UV absorbers. These compounds either do not absorb the desired wavelength or have only a small absorption or because of the necessary raw materials or the unproductive preparation processes are not as accessible as would be desirable.

The invention is therefore based on the object of making available improved UV absorbers.

The invention relates to compounds of the formula (I)

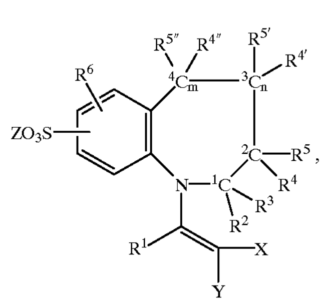

in which $R^1$ to $R^5$ (including $R^{4'}$, $R^{4''}$, $R^{5'}$, $R^{5''}$) independently of one another denote hydrogen, $C_1$–$C_8$-alkyl or $C_5$–$C_{10}$-cycloalkyl, with the proviso that two substituents on adjacent C atoms from the group consisting of $^1C$ to $^4C$ together can also together denote an optionally substituted polymethylene group, in particular $C_3$–$C_4$-alkylene, it being possible for a methylene group to be replaced by —O—, —S— or —NH—, $R^6$ denotes hydrogen, $C_1$–$C_8$-alkyl, $C_5$–$C_{10}$-cycloalkyl, hydroxyl, $C_1$–$C_8$-alkoxy, $COOR^{60}$, $CONR^{61}R^{62}$, $R^{60}$ to $R^{62}$ independently of one another denote hydrogen or $C_1$–$C_6$-alkyl, X, Y independently of one another denote hydrogen, CN, $CO_2R^{10}$, $CONR^{10}R^{11}$, $COR^{10}$ it being possible for one of the radials X or Y additionally to be a $C_1$–$C_8$-alkyl radical, a $C_5$–$C_{10}$-aryl radical, in particular phenyl, or a heteroaryl radical having 5 to 6 ring atoms (of these 1 to 2 hetero-atoms from the group consisting of N, O, S), where furthermore X and Y or $R^1$, together with one of the radicals X and Y, can denote the radical for the completion of a 5 to 7-membered ring which can contain up to 3 heteroatoms, in particular oxygen and/or nitrogen, it being possible for the ring atoms to be substituted (in particular with exocyclically doubly bonded oxygen (keto oxygen) and/or $C_1$–$C_8$-alkyl and/or $C_5$–$C_{10}$-cycloalkyl radicals) and/or to contain C═C double bonds, Z denotes hydrogen, ammonium, an alkali metal ion, in particular lithium, sodium potassium, ½ equivalents of alkaline earth metal ion, preferably calcium, magnesium or the cation of an organic nitrogen base employed for the neutralization of the free acid group, $R^{10}$, $R^{11}$ independently of one another denote hydrogen, alkyl, in particular $C_1$–$C_8$-alkyl or cycloalkyl, in particular having 5 to 10 ring atoms, and n, m independently of one another denote zero or 1.

The sulphonic acids according to the invention are particularly highly suitable for use in sunscreen compositions, preferably in cosmetic and pharmacological preparations. They are distinguished by very high absorption, excellent photostability and by a very low tendency for skin penetration.

Preferred compounds I are those in which $R^1$ to $R^6$ (including $R^{4'}$, $R^{4''}$, $R^{5'}$ and $R^{5''}$) denote hydrogen and n and m are zero.

Further preferred compounds I are those in which X denotes cyano and Y denotes carbo-$C_1$–$C_4$-alkoxy.

Further preferred compounds I are those in which the substituents X and Y, together with the carbon atom on which they are situated, denote a 2-methyl-4H-oxazol-5-one, an imidazoline-2,4-dione or cyclopentanone.

Particularly preferred compounds I correspond to the formulae

Ia

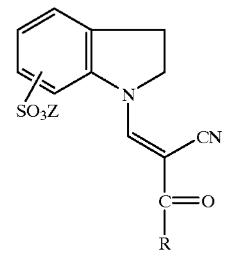

-continued

Ib

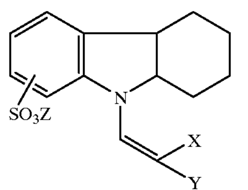

Ic

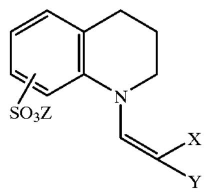

Id

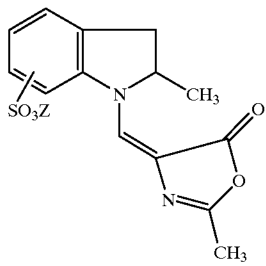

Ie

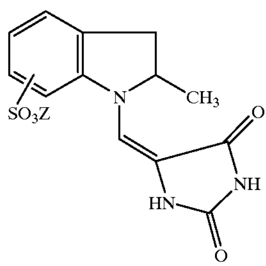

If

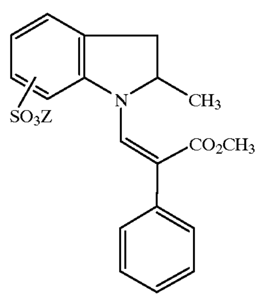

Ig

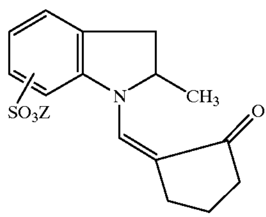

The compounds (I) can be obtained by sulphonation of the compounds (II)

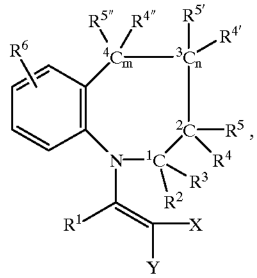

in which the substituents and indices have the meaning indicated above.

The compounds II and processes for their preparation are known in some cases (DE-OS [German Published Specification] 1 568 541, 3 519 926); insofar as they are not known, the compounds II can be prepared analogously to the known processes. As a rule, the corresponding cyclic secondary amine is condensed with a C—H-acidic component and a carboxylic acid ortho ester.

The sulphonation can be carried out using customary sulphonating agents. These include, for example, sulphuric acid, sulphur trioxide, oleum (preferably with $SO_3$ contents from 5 to 30% by weight), chlorosulphonic acid and—preferably—sulphuric acid and sulphuric acid/acetic anhydride mixtures.

The reaction can be carried out at temperatures from 0 to 200, preferably 20 to 120, in particular 30 to 80° C. For the reaction the sulphonating agents can be employed in stoichiometrically calculated amounts or in an excess; provided it is not wished to work with a large excess of sulphonating agent, the amounts of sulphonating agent in general are 1 to 4, preferably 1 to 2 equivalents, based on indoline II to be sulphonated. It is also possible to work in non-sulphonating solvents; in this case, those organic solvents are also suitable which are immiscible with water and act as entraining agents for water, such as, for example, methylene chloride, chloroform, toluene, ligroin, etc.

The sulphonation proceeds particularly mildly in solvents, i.e., for example, with sulphuric acid or sulphur trioxide in chloroform or liquid sulphur dioxide, with sulphuric acid/acetic anhydride in acetic acid or chlorosulphonic acid in chloroform.

In the sulphonation with chlorosulphonic acid, there is basically the choice of whether, by reaction with an equimolar amount of chlorosulphonic acid, the formation of the indolinesulphonic acid I is required directly or, with 2 mol of chlorosulphonic acid per mole of indoline, the formation of indoline sulphochloride is desired, from which the indolinesulphonic acid can then liberated by hydrolysis.

For the preparation of the compound I (X═CN), according to a particular embodiment compound II is reacted with sulphuric acid/acetic anhydride in acetic acid which leads to the resulting sulphonic acids precipitating out. These can then be separated off and an aqueous work-up and the formation of waste waters associated therewith thus avoided. If process variants are chosen in which the desired product does not precipitate, hydrolysis must be carried out; the products can then be obtained by evaporating the aqueous phase.

The invention thus further relates to a process for the preparation of the compounds I by the reaction of the compound II with sulphonating agents.

It was surprising that as a result of the sulphonation the absorption maxima are shifted to higher wavelengths, so that the products I according to the invention have absorption maxima of approximately 340 nm—thus just on the border between UV-A-I and UV-A-II.

The invention further relates to the use of the compounds I as UV absorbers, preferably in sunscreen compositions.

These UV absorbers have a fortunate combination of desirable properties, namely excellent photostability, toxicological and dermatological acceptability, excellent heat stability, very good solubility in cosmetic solvents (oils, water, glycols, alcohol, etc.), compatibility with cosmetic raw materials, pH stability, problem-free processability in cosmetic formulations and stability under use conditions, compatibility with packing materials, no colouring of textiles and it must be possible to wash out spots without problems, colourlessness and odour neutrality.

It is to be emphasized that cosmetic and pharmaceutical preparations with the new UV absorbers can also be stably formulated with low pH values without crystallization occurring.

The compounds according to the invention can be used as UV-A absorbers in cosmetic or pharmaceutical preparations which prevent the penetration of the UV rays through the applied film of the preparation. In general, this is the case when the cosmetic or pharmaceutical preparations contain 0.5 to 15, preferably 1 to 10, in particular 2 to 5, % by weight (based on the total weight of the preparation) of the compounds according to the invention.

The preparations comprising the compounds according to the invention can be used for the protection of the skin and of the hair—in particular hair already damaged by permanent waving, colouring and bleaching—from UV radiation. These cosmetic and pharmaceutical preparations used for the protection of the skin from UV radiation can be present in the use forms customarily used, i.e. as an oil-in-water or water-in-oil emulsion, as a milk, as a lotion or cream, aqueous or aqueous-alcohol gel or lotion, aerosol, hydrodispersion gel (emulsifier-free) or any other customary cosmetic or pharmaceutical preparation. For the protection of the hair from UV rays, preparations are preferably used as a shampoo, rinse, treatment, gel, lotion, spray or cream.

The cosmetic and pharmaceutical preparations can contain the constituents customarily used in these compositions such as, for example, emulsifiers, surface-active compounds, lanolin, petroleum jelly, water, triglycerides of fatty acids, polyethylene glycols, fatty alcohols, ethoxylated fatty alcohols, fatty acid esters (e.g. isopropyl palmitate, isooctyl stearate, diisopropyl adipate etc.), natural or synthetic oils or waxes, pigments (e.g. titanium dioxide, zinc oxide, pearl lustre pigments, colour pigments), thickening agents (e.g. hydroxyethylcellulose, bentonite, etc.), preservatives, geomectants, vitamins, silicone oils, glycerol, ethyl alcohol, perfume oils.

The compounds according to the invention can be employed in the corresponding preparations on their own or as a mixture; they can also be employed in combination with other UV absorbers—in particular UV-B absorbers for achieving a UV-A/B wide-band absorption, or with non-photostable UV absorbers (e.g. butylmethoxy-dibenzoylmethane, 4-isopropyldibenzoylmethane, 2-ethylhexyl p-dimethylaminobenzoate, 2-ethylhexyl and iso-amyl p-methoxycinnamate) for stabilization thereof. Examples of such compounds include:

p-aminobenzoic acid
ethyl p-aminobenzoate (25 mol) ethoxylated
2-ethylhexyl p-dimethylaminobenzoate
ethyl p-aminobenzoate (2 mol) N-propoxylated
glyceryl p-aminobenzoate
homomenthyl salicylate
2-ethylhexyl salicylate
triethanolamine salicylate
4-isopropylbenzyl salicylate
menthyl anthranilate
ethyl diisopropylcinnamate
2-ethylhexyl p-methoxycinnamate
methyl diisopropylcinnamate
isoamyl p-methoxycinnamate
p-methoxycinnamic acid diethanolamine salt
isopropyl p-methoxycinnamate
2-ethylhexyl 2-cyano-3,3-diphenylacrylate
ethyl 2-cyano-3,3'-diphenylacrylate
2-phenylbenzimidazolesulphonic acid and salts
N,N,N-trimethyl-4-(2-oxoborn-3-ylidenemethyl)-anilinium methylsulphate
tetraphthalylidene-dibornanesulphonic acid and salts
4-t-butyl-4'-methoxy-dibenzoylmethane
β-imidazole-4(5)-acrylic acid (urocaninic acid)
2-hydroxy-4-methoxybenzophenone
2-hydroxy-4-methoxybenzophenone-5-sulphonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methylbenzophenone
α-(2-oxoborn-3-ylidene)-tolyl-4-sulphonic acid and salts
3-(4'-methylbenzylidene)-d,1-camphor
3-benzylidene-d,1-camphor
4-isopropyldibenzoylmethane
2,4,6-trianilino-(p-carbo-2'-ethylhexyl-1'-oxy)-1,3,5-triazine.

Particularly suitable UV-B absorbers are:

2-ethylhexyl p-methoxycinnamate,
isoamyl p-methoxycinnamate,
2-phenylbenzimidazolesulphonic acid,
3-(4'-methylbenzylidene)-d,1-amphor,
2-ethylhexyl 2-cyano-3,3-diphenylacrylate and
2-ethylhexyl salicylate.

The combination of the compounds I with finely divided pigments, such as, for example, titanium dioxide, zinc oxide and iron oxide, in sunscreen and daily care products having UV protection is likewise possible.

EXAMPLES

Example 1

N-(β-Cyano-β-carbomethoxy-vinyl)-2-methylindoline-5-sulphonic acid

A mixture of 108 g (1.10 mol) of conc. sulphuric acid and 112 g (1.10 mol) of acetic anhydride was initially introduced into a stirring apparatus and treated at 30 to 40° C. in the course of 15 min with a solution of 134 g (0.55 mol) of N-(β-cyano-β-carbomethoxy-vinyl)-2-methylindoline in 400 g of acetic acid. The mixture was stirred further for approximately 15 to 20 min., during which the product precipitated from the reaction mixture. After filtering off, it was recrystallized from a mixture of isopropanol/water (3:1 parts by volume); 186 g of a product corresponding to a yield of 95% were obtained after drying (1 h/50° C.). Melting point: >270° C., λmax=339 nm, E1/1=1140.

Examples 2 and 3

The following compounds were prepared analogously to Example 1.

2. N-(β-β-Dicarbomethoxy-vinyl)-2-methylindoline-5-sulphonic acid λmax=338 nm, E1.1=1100.

3. N-(β-Acetyl-β-carbomethoxy-vinyl)-2-methylindoline-5-sulphonic acid λmax=350 nm, E1/1=1050

The compounds according to Example 1, 2 or 3 were used in the following examples.

Components Used:

30 DF: Aluminium distearate, supplier 14

Arlacel 165: Glyceryl stearate/polyethylene glycol (MW 100) stearate mixture, supplier 4

Arosol: Phenoxyethanol, supplier 1

Betone Gel MIO: Mineral oil, supplier 10

Carbopol 941: Polyacrylic acid, supplier 2

Carbopol ETD 2001: Acrylic acid copolymer, supplier 2

Cetiol OE: Dicapryl ether, supplier 3

Cetiol SN: Cetyl/stearyl isononanoate, supplier 3

Cremophor NP 14: Nonylphenol etherified with 14 mol of ethylene oxide, supplier 6

Cutina CBS: Glyceryl stearate, cetyl/stearyl alcohol, cetyl palmitate, coconut glycerides, supplier 3

Cutina FS 45: Palmitic/stearic acid mixture, supplier 3

Cutina MD: Glyceryl stearate, supplier 3

Dehyquart A: Cetyltrimethylammonium chloride, supplier 3

Eumulgin B 1: Cetyl/stearyl alcohol, etherified with 12 mol of ethylene oxide, supplier 3

Eumulgin B 2: Cetyl/stearyl alcohol, etherified with 20 mol of ethylene oxide, supplier 3

Heliopan, Type AV: Isooctyl p-methoxycinnamate, supplier 1

Heliopan,

Type E 1000: Isoamyl p-methoxycinnamate, supplier 1

Lanette O: Cetyl/stearyl alcohol mixture, supplier 3

Mulsifan RT 203/80 Fatty alcohol polyglycol ether, supplier 7

Myritol 318: Caprylic/capric triglyceride, supplier 3

Natrosol 250 HHR: Hydroxyethylcellulose, supplier 12

Neo Heliopan,

Type BB: 2-Hydroxy-4-methoxybenzophenone, supplier 1

Nutrilan L: Protein hydrolysate, Na salt, supplier 3

Phenonip: Mixture of p-hydroxybenzoic acid esters, supplier 9

Quaternium-18

Hectorit: Propylene carbonate, supplier 10

Solbrol P: Propyl p-hydroxybenzoate, supplier 5

Solbrol M: Methyl p-hydroxybenzoate, supplier 5

Neo Heliopan,

Type MBC: 4-Methylbenzylidene-camphor, supplier 1

Zinc oxide neutral: Zinc oxide, supplier 1

Neo Heliopan,

Type OS: Octyl salicylate, supplier 1

Neo Heliopan,

Type MA: Methylanthranilate, supplier 1

Uvinul P 25: Polyethylene glycol ester of p-aminobenzoic acid, supplier 6

Veegum Ultra: Magnesium aluminium silicate, supplier 11

Suppliers

1. Haarmann & Reimer GmbH, Holzminden
2. B. F. Goodrich Comp., Neuss
3. Henkel KGaA, Düsseldorf
4. ICI Speciality Chemicals, Frankfirt
5. Bayer AG, Leverkusen
6. BASF, Ludwisghafen
7. Zschimmer & Schwarz GmbH, Lahnstein
8. Nipa Lab. Ltd., Pontypridd Mid Glam, Wales, GB
9. Schülke & Mayr GmbH, Norderstedt
10. R. T. Vanderbilt Company Inc., Norwalk, USA
11. Hercules Inc., Wilmington, Del., USA

Example 4

A sunscreen lotion (O/W) of the following composition was prepared:

| | Constituents | % |
|---|---|---|
| A) | Cutina FS 45 | 2.00 |
| | Eumulgin B 1 | 0.25 |
| | Eumulgin B2 | 0.25 |
| | Cutina MD | 2.00 |
| | Lanette O | 2.80 |
| | Myritol 318 | 5.00 |
| | Liquid paraffin 65 cp | 3.00 |
| | Arosol | 0.80 |
| | Solbrol P | 0.10 |
| | Isooctyl p-methoxycinnamate | 3.00 |
| | Isoamyl p-methoxycinnamate | 3.00 |
| | Neo Heliopan, Type BB | 1.50 |
| B) | Water, dist. | 67.05 |
| | Carbopol 941 | 0.30 |
| | Sodium hydroxide, 10% strength in water | 2.45 |
| | 1,2-Propylene glycol | 2.00 |
| | Solbrol M | 0.20 |
| | UV-A absorber according to Example 1 | 4.00 |
| C) | Perfume oil | 0.30 |

Preparation:

Part A was fused at 75 to 80° C.

For the preparation of Part B, Carbopol was dispersed in water without lumps, dispersed with sodium hydroxide solution. The residual ingredients were then added and the mixture was heated to about 95° C.

Part B was then added to Part A with stirring and the mixture was cooled to room temperature. Part C was added at about 30° C.

Example 5

A sunscreen lotion (O/W) of the following composition was prepared:

| | Constituents | % |
|---|---|---|
| A) | Arlacel 165 | 3.00 |
| | Eumulgin B 2 | 1.00 |
| | Lanette O | 2.00 |
| | Myritol 318 | 4.00 |
| | Cetiol OE | 6.00 |
| | Betone Gel MIO and quaternium-18 hectorite | 3.00 |
| | Phenonip | 0.20 |
| | Cutina CBS | 2.00 |
| | Isooctyl p-methoxycinnamate | 7.00 |
| | 4-Methylbenzylidene-camphor | 1.00 |
| | Zinc oxide neutral | 5.00 |
| B) | Water, dist. | 57.90 |
| | Veegum Ultra | 1.00 |
| | Natrosol 250 HHR | 0.30 |
| | Glycerol 85% | 3.00 |

-continued

| Constituents | % |
|---|---|
| Phenonip | 0.30 |
| UV-A-absorber according to Example 1 | 3.00 |
| C) Perfume oil | 0.30 |

Preparation:

For the preparation of Part A, the components were fused at 80° C., mixed together and zinc oxide was added with dispersion.

For the preparation of Part B, the components were heated to 90° C. without Veegum and Natrosol, then these components were added with dispersion. Part B was then added to Part A with stirring and the mixture was cooled to room temperature. Part C was then added at 30° C. and the mixture was subsequently homogenized at a pH of 7.0–7.5.

Example 6

A sunscreen cream (O/W) of the following composition was prepared:

| Constituents | % |
|---|---|
| A) Cutina FS 45 | 2.00 |
| Eumulgin B 1 | 0.25 |
| Eumulgin B2 | 0.25 |
| Cutina MD | 2.00 |
| Lanette O | 3.00 |
| Myritol 318 | 5.00 |
| Cetiol SN | 3.00 |
| Arosol | 0.80 |
| Solbrol P | 0.10 |
| Isoamyl p-methoxycinnamate | 5.00 |
| Isooctyl p-methoxycinnamate | 3.00 |
| 4-Methylbenzylidenecamphor | 1.00 |
| Octyl salicylate | 3.00 |
| Butylmethoxydibenzoylmethane | 1.00 |
| B) Water, dist. | 60.90 |
| Carbopol 940 | 0.40 |
| Sodium hydroxide, 10% strength in water | 1.80 |
| 1,2-Propyleneglycol | 2.00 |
| Solbrol M | 0.20 |
| UV-A absorber according to Example 1 | 5.00 |
| C) Perfume oil | 0.30 |

Preparation:

The components of Part A were fused at 80° C. and mixed together. For the preparation of Part B, Carbopol was dispersed in water without lumps, then the residual constituents were added and the mixture was heated to about 90° C. Part B was then added to Part A with stirring and the mixture was cooled to room temperature. The addition of Part C was carried out at 30° C.

Example 7

A sunscreen gel of the following composition was prepared:

| Constituents | % |
|---|---|
| A) Ethyl alcohol | 5.00 |
| Water, dist. | 64.60 |
| 1,2-Propylene glycol | 5.00 |
| D-Panthenol | 0.50 |
| Carbopol ETD 2001 | 1.10 |
| B) Water | 5.00 |
| Triethanolamine | 2.30 |
| C) Neo Heliopan, Type Hydro, employed as a 30% strength solution after neutralization with triethanolamine/phenylbenzimidazolesulfonic acid; 10.00% corresponds to active substance: 3.00% | 10.00 |
| UV-A absorber according to Example 1 | 4.00 |
| D) Cremophor NP 14 | 1.20 |
| Perfume oil | 0.30 |

Preparation:

For the preparation of Part A, the individual constituents were dissolved in water, mixed together and Carbopol was added with dispersion without lumps. Triethanolamine (Part B) was then dissolved in water and added to Part A with stirring. After this, Part C and then Part D were added with stirring.

Example 8

A leave-on hair treatment of the following composition was prepared:

| Constituents | % |
|---|---|
| A) Water, dist. | 83.85 |
| Natrosol 250 HHR | 0.70 |
| Ethyl alcohol | 5.00 |
| Uvinul P 25 | 5.00 |
| UV-A absorber according to Example 1 | 1.00 |
| B) Nutrilan L | 2.00 |
| Dehyquart A | 0.20 |
| Phenonip | 0.50 |
| Triethanolamine | 0.25 |
| C) Mulsifan RT 203/80 | 1.20 |
| Perfume oil | 0.30 |

Preparation:

For the preparation of Part A, water was heated to about 85° C., Natrosol was scattered in and the mixture was cooled to room temperature with vigorous stirring. Subsequently, the residual constituents of Part A, then the Parts B and then the Parts B and C were added.

We claim:

1. An UV absorber comprising a compound of the formula (I)

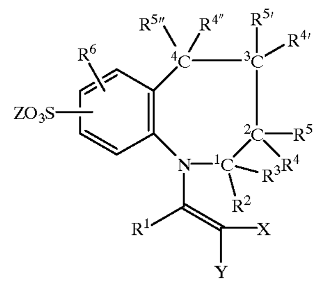

wherein $R^1$, $R^2$, $R^3$, $R^{4'}$, $R^{4''}$, $R^{5'}$, $R^{5''}$ are, each independently, hydrogen, $C_1$–$C_8$-alkyl or $C_5$–$C_{10}$-cycloalkyl, or wherein two substituents on adjacent C atoms from the group consisting of $^1C$ to $^4C$ together can also together form a substituted or unsubstituted polymethylene group, and wherein a methylene group in the polymethylene goup can be replaced by —O—, —S— or —NH—;

$R^6$ is hydrogen, $C_1$–$C_8$-alkyl, $C_5$–$C_{10}$-cycloalkyl, hydroxyl, $C_1$–$C_8$-alkoxy, $COOR^{60}$, $CONR^{61}R^{62}$, where $R^{60}$ to $R^{62}$ are, each independently, hydrogen or $C_1$–$C_6$-alkyl;

X and Y are, each independently, hydrogen, CN, $CO_2R^{10}$, $CONR^{10}R^{11}$, or $COR^{11}$, where $R^{10}$, $R^{11}$ are, each independently, hydrogen, $C_1$–$C_8$-alkyl or $C_5$–$C_{10}$-cycloalkyl;

or where one of X or Y is a $C_1$–$C_8$-alkyl radical, a $C_5$–$C_{10}$-aryl radical, or a heteroaryl radical having 5 to 6 ring atoms and having 1 or 2 heteroatoms selected from the group consisting of N, O, and S, or where $R^1$, together with one of X or Y, form a 5 to 7-membered ring which can contain up to 3 heteroatoms, and wherein the ring can be substituted with C═C double bonds, contain C═C double bonds, or both;

Z is hydrogen, ammonium, an alkali metal ion, ½ equivalents of alkaline earth metal ion, or the cation of an organic nitrogen base employed for the neutralization of the free acid group; and n and m are, each independently, 0 or 1.

2. A sunscreen composition comprising a compound of the formula (I)

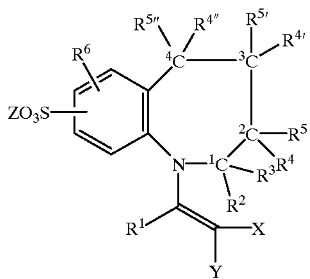

wherein $R^1$, $R^2$, $R^3$, $R^{4'}$, $R^{4''}$, $R^{5'}$, $R^{5''}$ are, each independently, hydrogen, $C_1$–$C_8$-alkyl or $C_5$–$C_{10}$-cycloalkyl, or wherein two substituents on adjacent C atoms from the group consisting of $^1C$ to $^4C$ together can also together form a substituted or unsubstituted polymethylene group, and wherein a methylene group in the polymethylene goup can be replaced by —O—, —S— or —NH—;

$R^6$ is hydrogen, $C_1$–$C_8$-alkyl, $C_5$–$C_{10}$-cycloalkyl, hydroxyl, $C_1$–$C_8$-alkoxy, $COOR^{60}$, $CONR^{61}R^{62}$, where $R^{60}$ to $R^{62}$ are, each independently, hydrogen or $C_1$–$C_6$-alkyl;

X and Y are, each independently, hydrogen, CN, $CO_2R^{10}$, $CONR^{10}R^{11}$, or $COR^{10}$, where $R^{10}$, $R^{11}$ are, each independently, hydrogen, $C_1$–$C_8$-alkyl or $C_5$–$C_{10}$-cycloalkyl;

or where one of X or Y is a $C_1$–$C_8$-alkyl radical, a $C_5$–$C_{10}$-aryl radical, or a heteroaryl radical having 5 to 6 ring atoms and having 1 or 2 heteroatoms selected from the group consisting of N, O, and S, or where $R^1$, together with one of X or Y, form a 5 to 7-membered ring which can contain up to 3 heteroatoms, and wherein the ring can be substituted with C═C double bonds, contain C═C double bonds, or both;

Z is hydrogen, ammonium, an alkali metal ion, ½ equivalents of alkaline earth metal ion, or the cation of an organic nitrogen base employed for the neutralization of the free acid group; and n and m are, each independently, 0 or 1.

3. The sunscreen composition of claim 2, further comprising emulsifiers, surface-active compounds, lanolin, petroleum jelly, water, triglycerides of fatty acids, polyethylene glycols, fatty alcohols, ethoxylated fatty alcohols, fatty acid esters, natural or synthetic oils or waxes, pigments, thickening agents, preservatives, geomectants, vitamins, silicone oils, glycerol, ethyl alcohol, or perfume oils.

4. The compositions of claim 2, comprising 0.5 to 15% by weight, based on the total weight of the composition, of the compound (I).

5. The compositions of claim 2, comprising 1 to 10% by weight, based on the total weight of the composition, of the compound (I).

6. The compositions of claim 2, comprising 2 to 5% by weight, based on the total weight of the composition, of the compound (I).

* * * * *

UNITED STATES PATENT AND TRADEMARK OFFICE

CERTIFICATE OF CORRECTION

PATENT NO. : 6,042,814

DATED : March 28, 2000

INVENTOR(S) : Oskar Koch et al.

It is certified that error appears in the above-identified patent and that said Letters Patent is hereby corrected as shown below:

On the Title Page

In column 1, before line 1, under "U.S. PATENT DOCUMENTS", insert --3,079,366 2/1963 Boyle et al.--

In the Specification

In column 11, line 3, delete "goup" and substitute --group-- in its place.

In column 11, line 10, delete "$COR^{11}$," and substitute --$COR^{10}$,-- in its place.

In column 12, line 3, delete "goup" and substitute --group--.

Signed and Sealed this

Eighth Day of May, 2001

Attest:

NICHOLAS P. GODICI

Attesting Officer

*Acting Director of the United States Patent and Trademark Office*